United States Patent [19]

Growdon et al.

[11] Patent Number: 4,609,647

[45] Date of Patent: Sep. 2, 1986

[54] CYTIDYL DIPHOSPHOCHOLINE-DRUG COMPOSITION AND PROCESS

[75] Inventors: John H. Growdon, Brookline; Richard J. Wurtman, Boston, both of Mass.

[73] Assignee: Massachusetts Institute of Technology, Cambridge, Mass.

[21] Appl. No.: 785,928

[22] Filed: Oct. 9, 1985

Related U.S. Application Data

[63] Division of Ser. No. 738,001, May 28, 1985, abandoned, which is a continuation-in-part of Ser. No. 366,888, Apr. 8, 1982, Pat. No. 4,430,330, which is a continuation of Ser. No. 229,894, Jan. 30, 1981, abandoned, which is a continuation of Ser. No. 126,124, Feb. 29, 1980, abandoned, which is a continuation-in-part of Ser. No. 88,227, Oct. 25, 1979, abandoned, which is a continuation of Ser. No. 847,967, Nov. 2, 1977, abandoned.

[51] Int. Cl.$^4$ ............................................ A61K 31/685
[52] U.S. Cl. ........................................................ 514/78
[58] Field of Search ............................................ 514/78

Primary Examiner—Stanley J. Friedman
Attorney, Agent, or Firm—Paul J. Cook

[57] ABSTRACT

Cytidyl diphosphocholine is administered to a patient alone to increase brain acetylcholine levels or concomitantly with a drug in order to potentiate the effect of the drug by increasing acetylcholine levels in the brain or other tissues, and/or to suppress, or block the development of, unwanted side effects of the drug, by increasing acetylcholine levels in the brain or other tissues.

1 Claim, No Drawings

CYTIDYL DIPHOSPHOCHOLINE-DRUG COMPOSITION AND PROCESS

REFERENCES TO RELATED APPLICATIONS

This is a division of Ser. No. 738,001, filed 5/28/85, now abandoned, which is a C-I-P of Ser. No. 366,888, filed 4/8/82, now U.S. Pat. No. 4,430,330, which is a continuation of Ser. No. 229,894, filed 1/30/81, now abandoned, which is a continuation of Ser. No. 126,124, filed 2/29/80, now abandoned, which is a C-I-P of Ser. No. 88,227, filed 10/25/79, which is a continuation of Ser. No. 847,967, filed 11/2/77, both now abandoned.

BACKGROUND OF THE INVENTION

This invention relates to a process and composition for the administration of cytidyl diphosphocholine (CDP choline) that dissociates to form choline, along with a drug, in order to treat human disorders by increasing acetylcholine levels in brain and other tissues.

There are a number of diseases which affect acetylcholine-containing neurons in the brain or other tissues, and which are treated by drugs that cause undesired side effects by diminishing acetylcholine's release; there also exist diseases now treated by other drugs in which the potency and/or efficacy of the drugs could be improved by combining them with a source of choline in order thereby to enhance the release of acetylcholine. Such diseases include both those primarily involving the brain including diseases of higher cortical functions, psychiatric illnesses, movement disorders, old age, senility, Alzheimer's disease, Tardive dyskinesia, Parkinson's disease; certain affective disorders including mania, ataxias including Friedreich's ataxia, the dyslexias, the behavioral and neurological syndromes seen after brain trauma and/or anoxia, and those involving the peripheral nervous system, e.g., neuromuscular disorders such as myasthenia gravis as well as post stroke rehabilitation. Tardive dyskinesia, for example, is a particularly common movement disorder associated with inadequate release of brain acetylcholine as a result of drug administration for the initial brain disease (e.g., psychosis). Tardive dyskinesia is a choreic movement disorder characterized by involuntary twitches in the tongue, lips, jaw and extremities. It typically occurs in susceptible persons after chronic ingestion of neuroleptic drugs and may involve an imbalance in the postulated relation between dopaminergic and cholinergic neurons and the basal ganglions. Thus, drugs that either block catecholamine synthesis (e.g., alpha-methyl-p-tryosine), deplete the brain of monoamines (e.g., reserpine, tetrabenazine) or phenothiazines, haloperidol) often suppress tardive dyskinesia, whereas drugs that indirectly stimulate dopamine receptors (e.g. amphetamine, levodopa) often exacerbate the abnormal movements. Drugs assumed to increase the amount of acetylcholine within brain synapses (e.g., physostigmine, deanol), also tend to suppress the chorea of tardive dyskinesia, whereas anticholinergics (e.g., scopolamine), make it worse.

Not all choline analogues result in an increase in brain choline levels when administered to an animal. For example, deaonl is a choline analogue which does not cause increased brain choline levels. However, when choline is administered by injection or by dietary supplementation increased blood choline levels in the rat results; this, in turn, increases choline levels in cholinergic neurons within the brain and elsewhere in the body, thereby accelerating the synthesis of acetylcholine, increasing tissue acetylcholine levels, and increasing the amounts of acetylcholine released into brain synapses. In human beings, oral doses of choline or of lecithin, a naturally-occurring compound that dissociates to choline, were found to cause dose-related increases in blood choline levels of sufficient magnitude (based on the studies on rats) to enhance brain acetylcholine synthesis and release; choline levels in the cerebrospinal fluid also rose in parallel. It has also been reported in four human patients that the administration of choline decreased the choreiform movements of tardive dyskinesia; no data were provided as to whether or not the drug given concurrently for psychosis (haloperidol, 3 mg per day) continued to be effective during the brief period of choline administration, and it was concluded that the apparent effectiveness of choline had to be interpreted with caution, since ". . . all four patients with tardive dyskinesia could have been gradually improving during the study" since this disease is characterized by extreme variability of clinical course. Thus, prior to this invention, it was known that choline and some choline analogues can be utilized to increase brain choline levels while other choline analogues do not result in increased brain choline levels.

SUMMARY OF THE INVENTION

This invention is based upon the discovery that cytidyl diphosphocholine (CPD choline), when administered concomitantly with a drug, can, by increasing neuronal acetylcholine levels, (1) reduce or prevent undesirable side effects of the drug associated with inadequate acetylcholine release, and/or (2) potentiate the effectiveness of the drug. The CDP choline and drug may be administered orally such as in tablet, capsule or liquid form or parenterally by intravenous, intramuscular or subcutaneous injection. The process of this invention is useful even with patients having a prior history of the undesirable side effect or of suboptimal therapeutic response, or of therapeutic responses requiring a very large drug dose, but who continue taking the drug.

DETAILED DESCRIPTION OF SPECIFIC EMBODIMENTS

In accordance with this invention, CDP choline is orally administered to a patient alone or prior to or together with a drug in order to increase blood levels of choline, and thereby to increase the level of acetylcholine in the brain. The acetylcholine is synthesized from choline and acetyl CoA in a reaction catalyzed by choline acethyltransferase (CAT). It has been found that the administration of CDP choline potentiates the drug by reducing the incidence or suppressing side effects of the primary drug and/or that lower dosages of the primary drug are needed to attain the desired effects of the drug. While the results obtained will vary from patient to patient, the reduced side effects and increased efficacy observed are sufficiently significant as to justify the conclusion that their reduction is caused by administration of CDP choline. It is surprising that the administration of CDP choline results in increased levels of brain choline since CDP choline is known to be incorporated directly by cells into their own membrane lecithin. Hence, it would be anticipated that the gut cells would utilize the CDP choline rather than breaking it down to liberate choline.

There are a number of brain and peripheral diseases involving cholinergic neurons that are presently treated with drugs that are only sometimes effective, or that require very large doses of the drugs (with correspondingly greater cost and incidence of side effects); some of these diseases can be more effectively treated by combining the existing drug therapy with concomitant choline or natural or synthetic compounds that dissociated to form choline. One example is the mania phase of manic-depressive psychoses, which is currently treated with lithium salts. These salts, as a biochemical side effect, interfere with the uptake of choline into the brain; this tends to reduce brain acetylcholine levels, which exacerbates the mania. The co-administration of CDP choline with the lithium salts would allow more effective treatment of the mania, and a reduction in the lithium dose needed by most patients. Another example is myasthenia gravis, a peripheral disease involving the cholinergic nerves that innervate skeletal muscle. The current mode of treatment involves giving drugs like neostigmine (Protigmin) that increase acetycholine levels in neuromuscular synapses by blocking the degradation of this neurotransmitter. Were CDP choline, a compound that dissociates to form choline, to be given concomitantly with the choline-sterase-inhibitor, the resulting increases in acetylcholine levels would both potentiate the effect of the cholinesterase-inhibitor and allow for a reduction in its dose. When CDP choline is administered alone, it is useful in treating the following disorders which may be associated with inadequate release of acetylcholine; old age, senility, Alzheimer's disease, tardive dyskinesia, Parkinson's disease, certain effective disorders including mania, ataxias including Freidreich's ataxia, the dyslexias, the behavioral and neurological syndromes seen after brain trama and/or anoxic, and peripheral neuromuscular disorders including myasthenia gravis and post-stroke rehabilitation.

Some of the drugs utilized in the present invention are those which cause significant undesirable effects. Representative of such drugs are neuroleptics, such as the phenothiazines including thioridozine (MELLARIL ®), fluphenazine (PROLIXIN ®), trifluoperazine and chlorpromazine (THORAZINE ®); the thioxanthenes including chlorprothixene (TARACTON ®) and thiothixene (NAVANE ®); the butyrophenones including haloperidol (HALDOL ®) and indolic compounds including molindone (MOBAN ®) that are used in the treatment of such diseases as schizophrenia, Huntington's disease and Tourette's syndrome. Other drugs that caused undesired effects include psychomotor stimulants such as amphetamine (DEXADRINE ®) and methylphenidate (RITALIN ®) that are used to treat patients with minimal brain dysfunction, hyperactivity and specific dyslexias.

The effects of some other drugs utilized in this invention are potentiated. Representative of such drugs are: (1) isoxsuprine (VASODILAN ®) and dihydroergotamines (HYDERGINE ®) or piracetem or the like that are used in the treatment of senility; (2) gluco-corticosteroids such as triamcinotone (ARISTOCORT ®) and predinsone (METICORTEN ®) and anti-choline-sterase drugs such as neostigmine (PROSTIGMIN ®) aind pyridostigmine (MESTINON ®) that are used to treat neuromuscular diseases, including polymyositis and myasthenia gravis; (3) lithium (ESKALITH ®) that is used to treat manic-depressive illness and (4) tranquillizers such as phenobarbitol (LUXINAL ®) and diazepam (VALIUM ®) that are used to treat anxiety psychoneurosis.

The CDP choline is administered so that a choline level of at least about 20–30 nanomoles/ml and usually between about 10 and 50 n moles/ml is attained in the patient's bloodstream. For example, when administering CDP choline in the form of capsules or tablets, suitable dosages are from about 1 to 30 g/day, preferably 3–20 g/day taken in divided doses 500 to 1000 mg/cap or tab. When CDP choline is administered in liquid form admixed with a conventional liquid carrier such as a sweetened elixir or the like, from about 1 to 10 grams/15 ml, preferably from about 2 to 5 grams/15 ml can be utilized.

In the process of this invention, the CDP choline is administered alone or prior to or concomitantly with the drug. When administered prior to the drug, the period of time between CDP choline administration and drug administration must be less than when acetylchlorine concentration reduction begins to occur in the brain. Generally, the period of time between administrations is less than about 36 hours, preferably less than about 24 hours.

The following example illustrates the present invention and is not intended to limit the same.

EXAMPLE I

This example illustrates that CDP choline, when administered to laboratory rats causes an increase in blood plasma and brain choline levels. In this study, the effects of CDP choline (2.25 g/kg body weight) were compared to the effects of equimolar choline chloride or phosphatidylcholine (PC) on plasma choline levels in rats with jugular cannulas. CDP choline elevated plasma choline levels by 50% after 4 hours; its time course being more similar to PC than to choline chloride.

In a separate experiment, whole brain choline levels in rats were measured. Laboratory rats were given CDP choline (1.5 g/kg body weight) or equimolar choline chloride and were killed after 1, 5 and 24 hours by focussed microwave irradiation to the head as were controls which were not administered choline chloride or CDP choline. Whole brain choline was elevated relative to controls at all times and at all times tested in both choline treated and CDP choline treated animals. Peak values of choline occurred at 5 hours. Choline levels returned near baseline by 24 hours. Since administration of CDP choline raises brain choline, brain acetylcholine levels also are raised, Cohen et al, *Life Sciences*, 16:1095–1102, 1975, and thereby caudate tyrosine hydroxylase is activated, Ules et al, *Science*, 194:1060–1061, 1976.

We claim:

1. The process of treating a human patient afflicted with a condition associated with inadequate release of brain acetylcholine which comprises administering to the patient cytidyl diphosphocholine at a dosage sufficient to increase brain choline levels and blood levels of choline to between about 10 to 50 n moles/ml.

* * * * *